United States Patent
Pirotte

(10) Patent No.: US 9,247,732 B2
(45) Date of Patent: Feb. 2, 2016

(54) AGROCHEMICAL FORMULATIONS CONTAINING A COMPATIBILITY AGENT

(76) Inventor: Alan Pirotte, Houffalize (BE)

( * ) Notice: Subject to any disclaimer, the term of this patent is extended or adjusted under 35 U.S.C. 154(b) by 0 days.

(21) Appl. No.: 14/116,720

(22) PCT Filed: May 10, 2011

(86) PCT No.: PCT/EP2011/057524
§ 371 (c)(1),
(2), (4) Date: Dec. 5, 2013

(87) PCT Pub. No.: WO2012/152318
PCT Pub. Date: Nov. 15, 2012

(65) Prior Publication Data
US 2014/0088198 A1    Mar. 27, 2014

(51) Int. Cl.
*A01N 25/22*    (2006.01)
*A01N 47/44*    (2006.01)

(52) U.S. Cl.
CPC ............... *A01N 25/22* (2013.01); *A01N 47/44* (2013.01)

(58) Field of Classification Search
CPC .................................................. A01N 25/22
See application file for complete search history.

(56) References Cited

U.S. PATENT DOCUMENTS

| 3,312,589 | A * | 4/1967 | Entley et al. ............... | 514/385 |
| 6,462,052 | B1 * | 10/2002 | Duvert et al. ............... | 514/275 |
| 2014/0148510 | A1 | 5/2014 | Pirotte | |
| 2014/0193503 | A1 | 7/2014 | Pirotte | |

FOREIGN PATENT DOCUMENTS

DE    3248115 A1    6/1984
FR    2 074 655    10/1971

OTHER PUBLICATIONS

Somers, E., et al. "Effect of Dodine Acetate on the Electrophoretic Mobility of Neurospora crassa Conidia." J. gen. Microbiol. (1967), vol. 48, pp. 147-154.*
Pfannkoch, E. "The Preparation of Buffers and Other Solutions: A Chemist's Perspective." Molecular Biology Problem Solver: A Laboratory Guide. (c) 2001. Edited by Alan S. Gerstein.*
International Search Report and Written Opinion of the International Searching Authority for International Application No. PCT/EP2011/057524, mailed on Oct. 4, 2011.
Dodine, "The pesticide manual ED—Worthing C R, Hance R J", Pesticide Manual. World Compendium; [Pesticide Manual], Farnham, BCPC, GB, p. 382 (Jan. 1, 1995).
"Material Safety Data Sheet, Equal 65 WP (Dodine 65 WP)," Norac Concepts Inc, pp. 1-3 (Nov. 19, 2007). Retrieved from the Internet: URL:http://www.bartlett.ca/Bartlett/nmb/MSDSLabel.nsf/33679510e3c80d96852574a20055f364/0cge5ecdd7d4490385256bba006a99b3/$FILE/Equal 65WP msds english.pdf [retrieved on Sep. 21, 2011].
Dodine, "The pesticide manual ED—Worthing C R, Hance R J", Pesticide Manual. World Compendium; [Pesticide Manual], Farnham, BCPC, GB, pp. 382-383 (Jan. 1, 1995).

* cited by examiner

*Primary Examiner* — Noble Jarrell
*Assistant Examiner* — John S Kenyon
(74) *Attorney, Agent, or Firm* — Carmody Torrance Sandak & Hennessey LLP

(57) ABSTRACT

Agrochemical compositions are described which contain a carboxylic acid salt of dodecylguanidine and a compatibility agent for slowing down the dissociation reaction of the carboxylic acid salt of dodecylguanidine in an aqueous medium. Also, the formation of anionic dodecylguanidine is suppressed or prevented. The ratio of the dodecylguanidine acetate to that of the compatibility agent in the agricultural compositions is below 5.0, preferably between 3.0 and 0.5, more preferably equals 1.4.

18 Claims, No Drawings

AGROCHEMICAL FORMULATIONS CONTAINING A COMPATIBILITY AGENT

CROSS-REFERENCE TO RELATED APPLICATIONS

This application is the U.S. National Phase under 35 U.S.C. §371 of International Application PCT/EP2011/057524, filed May 10, 2011.

TECHNICAL FIELD

The invention relates generally to the field of agricultural chemistry, and more specifically to compatibility agents for improving the stability and uniformity of aqueous mixtures of carboxylic acid salt of dodecylguanidine.

BACKGROUND

Relative to certain crops, such as apples and cherries, it is desirable to effect spraying of both an insecticide and fungicide simultaneously because of the simultaneous appearance of the pests which are to be destroyed. In this respect, tank mixing two or more pesticides and/or fertilizers is a convenient way to reduce labour and equipment use. In addition, adjuvants may be added.

Tank mixing chemicals is a convenient way to reduce labour and equipment use, it offers flexibility and may increase pesticide effectiveness. However, an incompatible mix can cause equipment damage, downtime, damage to desirable plants and chemical ineffectiveness. Incompatible mixes can result from chemical or physical incompatibility. Chemical incompatibility occurs when one or more of the chemicals changes properties. Physical incompatibility causes the formation of lumps or gels. The chemicals do not disperse properly and settle out of suspension. Incompatibility can also take the form of foams, stratification in the tank, colour changes and bubbles.

Dodecylguanidine acetate, known as dodine, is a fungicide recommended for the control of a number of major fungal diseases on cash crops such as apples and bananas. It is known in the art that dodine is incompatible with some pesticides and/or additives.

For instance, in U.S. Pat. No. 3,452,931 it was disclosed that dodine and a material known under the trademark Glyodin are immiscible and therefore cannot be mixed before spraying. An agricultural sprayer was disclosed which is capable of the simultaneous but separated application of dodine and Glyodin. Whereas this liquid sprayer offers a solution to the compatibility issue of dodine, it is desirable that an applicator would not have to resort to special equipment.

There remains a need in the art for providing further solutions that resolve the incompatibility of dodine with tank mix partners.

The present invention aims to resolve or ameliorate at least some of the problems mentioned above. In particular, the invention thereto aims to provide a compatibility agent for dodine that resolves the incompatibility of dodine in a tank-mix.

SUMMARY OF THE INVENTION

The present invention relates to an agrochemical composition comprising a carboxylic acid salt of dodecylguanidine and a compatibility agent for slowing down the dissociation reaction of the carboxylic acid salt of dodecylguanidine in an aqueous medium thereby suppressing or preventing the formation of anionic dodecylguanidine, characterized in that, the ratio of the dodecylguanidine acetate to the acetate anion in the composition is below 5.0, preferably between 3.0 and 0.5, more preferably equals 1.4.

In a second aspect, the invention relates to a tank-mix prepared by mixing water, an agrochemical composition comprising a carboxylic acid salt of dodecylguanidine, preferably dodecylguanidine acetate (dodine), a compatibility agent for slowing down the dissociation reaction of the carboxylic acid salt of dodecylguanidine in an aqueous medium thereby suppressing or preventing the formation of anionic dodecylguanidine, and an active ingredient selected from the list of pesticides, fertilizers, biocides and combinations thereof, characterized in that, the ratio of the dodecylguanidine acetate to the alkali metal acetate anion or earth alkali metal acetate anion in the tank-mix is below 5.0, preferably between 3.0 and 0.5, more preferably equals 1.4.

By the term "active ingredient" as used herein, is meant an ingredient that is chemically active and/or biologically active in origin. The activity is directed against a pest, particularly a plant pest. In this regard an "active ingredient" ingredient can be a single ingredient or a combination of ingredients.

In a further aspect, the invention provides a method for preparing an aqueous tank-mix of a carboxylic acid salt of dodecylguanidine, comprising the steps of:
  adding to the tank an amount of compatibility agent for slowing down the dissociation of the carboxylic acid salt of dodecylguanidine to form anionic dodecylguanidine, wherein the amount of compatibility agent is selected so that the ratio of the dodecylguanidine acetate to that of the compatibility agent is below 5.0, preferably between 3.0 and 0.5, more preferably equals 1.4,
  adding a carboxylic acid salt of dodecylguanidine to a spray tank holding water, and
  adding to the aqueous mixture an active ingredient selected from the list of pesticides, fertilizers, biocides and combinations thereof, to obtain an aqueous tank-mix.

By the term "aqueous" as used herein, is meant that the solvent used in the composition is mainly water. Hence, "aqueous" and "water-based" may be considered synonyms. Water-based formulations generally have the advantage that they require little or no organic solvent fraction.

In a final aspect, the invention provides a use of an alkali metal acetate or earth alkali metal acetate for improving the compatibility of a carboxylic acid salt of dodecylguanidine or of dodecylguanidine hydrochloride with an additional pesticide and/or fertilizer in an aqueous medium.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

The present invention relates to a compatibility agent for formulations comprising a carboxylic acid salt of dodecylguanidine. Preferably said formulations are agrochemical or biocide formulations.

By the term "dodecylguanidine" a structure according to formula (1) is meant,

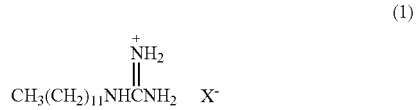

(1)

wherein X represents an acid residue of a monocarboxylic acid such as acetic, propionic, capric, stearic, benzoic, and naphtoic; or a dicarboxylic acid such as malonic or succinic acid or hydrohalogenide. Preferably the hydrohalogenide is hydrochloride.

In a preferred embodiment of the invention, the carboxylic acid is a monocarboxylic acid. In a preferred embodiment, the carboxylic acid salt is an alkali metal acetate or earth alkali metal acetate, preferably sodium acetate.

In a preferred embodiment, the carboxylic acid salt of dodecylguanidine is dodecylguanidine mono acetate, known as dodine or 1-dodecylguanidinium acetate.

Dodine is a fungicide and bactericide. By the term "fungicide" as used herein, is meant any toxin used to kill or inhibit growth of fungi.

Dodine is particularly efficacious against the fungal diseases almond scab; apple and pear scab; banana sigatoka; cherry leaf spot; peach leaf curl; olive leaf spot; peanut early and late leaf spot; pecan scab, liver spot, brown and downy leaf spot, leaf blotch and downy mildew; and walnut anthracnose. By the term "fungicidal disease" as used herein, is meant a disease caused by a fungus.

Dodine is registered for foliar use on pome fruits, stone fruits including cherries, and nuts including walnuts. For apple scab it is applied from the budding of flowers to flowering and late in the season before harvest. Because of this relatively broad window of application, interest is high to apply dodine together with other pesticides and/or fertilizers and to add dodine to aqueous mixtures comprising other pesticides and/or fertilizers, so called tank-mixes, before application on the crop.

In a combination with many other pesticides, fertilizers and additives, dodine is poorly compatible or incompatible. By the term "compatible" as used herein, it is meant herein that no adverse effects occur as a result of mixing them together.

Dodine is an amphiphilic molecule consisting of a hydrophobic apolar group, the $C_{12}$ hydrocarbon chain, and a hydrophilic polar head group, the guanidine part, bound to an acetate group. In solution, the acetate group dissociates from the dodecylguanidine group. Consequently dodecylguanidine becomes positively charged, and cationic. The cationic dodecylguanidine may then physically interact with components that are negative charged, i.e. anionic. In tank-mixes, compounds are often present that are anionic. For instance, sodium lignosulphonate is often present in tank-mixed pesticides partners for a carboxylic acid salt of dodecylguanidine, in particular dodine. Lignosulphonate dispersants are often present in wettable powder and wettable granule formulations. Alternative dispersants, albeit also anionic, are alkylnaphtalene sulphonates, for instance sodium diisopropylnaphtalene sulphonate and sodium alkylnaphtalene sulphonate. In such cases, precipitation of dodecylguanidine occurs due to a physical incompatibility between cationic dodecylguanidine and negatively charged components present, such as lignosulphonates or alkylnaphtalene sulphonates.

The inventors have found that the physical incompatibility can be overcome by the addition of a compatibility agent. The inventors have found that alkali metal acetates and/or earth alkali metal acetates improve the compatibility of a carboxylic acid salt of dodecylguanidine with an additional pesticide and/or fertilizer in an aqueous medium.

The addition of the alkali metal acetate and/or earth alkali metal acetates displaces the chemical equilibrium as depicted in the following equation (2):

(2)

The cationic dodecylguanidine makes a chemical bond with the carboxylic acid anions present in solution. A carboxylic acid salt of dodecylguanidine is formed. The solubility of dodecylguanidine is decreased by making a physical bond with the acetate in solution. However, in this way, dodine is more stable in the presence of other components. The compatibility of carboxylic acid salt of dodecylguanidine, in particular dodine, is improved by the addition of the acetate anion.

The inventors have found that acetate anion acts as a compatibility agent for dodine. With the term "compatibility agent" as used herein, it is meant an adjuvant that allows easier mixing of two or more components in a solution, thereby allowing the use of two or more chemicals in a tank that would otherwise be incompatible.

Test protocols for evaluating the compatibility of pesticide active ingredients and adjuvants are readily available and known to a person skilled in the art. A method suitable for use in the present invention is as follows: fill a 250 ml beaker with 200 ml of well water (temperature 15-17° C., water hardness 8° dH corresponding to 80 mg calcium oxide/l). Add an agrochemical formulation to the water in an amount corresponding to the application rate, e.g. 1.25 ml of Dodine 400 SC–Syllit®. Add a magnetic stirrer to the beaker. Stir the suspension for approximately 5 minutes at a speed of rotation of 700 rotations per minute. Add a mixing partner, such as an adjuvant or second plant protection product to the suspension. Stir the suspension for an additional 15 minutes. Stop stirring when a total stirring time of 20 minutes is obtained. Let the suspension stand unstirred for a few minutes. Then check for any separation, sediment, crystallization or flocculation. Note down the results of the visual observation. Stir the suspension for a further 20 minutes. Stop the stirring. After 2 hours have lapsed assess the compatibility for a second time. Upon finishing the second observation, pour the whole suspension over a 100 μm sieve. Note down if residue is present on the sieve.

In a preferred embodiment, the ratio of the carboxylic acid salt of dodecylguanidine to the compatibility agent is below 5.0, preferably between 3.0 and 0.5, more preferably equals 1.4.

The ratio is calculated as the amount, expressed in weight, of the carboxylic acid salt of dodecylguanidine to the amount, expressed in weight, of the stabilizing agent.

Preferred compatibility agents are alkali metal acetates, earth alkali metal acetates, and mixtures thereof. A particularly preferred stabilizing agent is sodium acetate. If more than one stabilizing agent is present, the total amount, expressed in weight of the stabilizing agent is used in the calculation.

In a preferred embodiment of an agrochemical composition of the invention, the carboxylic acid salt of dodecylguanidine is dodecylguanidine acetate (dodine) and the compatibility agent is an alkali metal acetate or earth alkali metal acetate, preferably sodium acetate.

Preferably the compatibility agent for the carboxylic acid salt of dodecylguanidine is already build-in the dodecylguanidine formulation. The compatibility agent can be built into a formulation comprising a carboxylic acid salt of dodecylguanidine.

Wettable powder, wettable granules or suspension concentrate are preferred formulations for active ingredients with poor water solubility. For example, dodine has a solubility of 0.63 g/l at 25° C. In a preferred embodiment, the alkali metal acetate and/or earth alkali metal acetate is comprised in a formulation of the carboxylic acid salt of dodecylguanidine which is in the form of a wettable powder (WP), wettable granules (WG) or a suspension concentrate (SC). This has the advantage that the compatibility agent is readily available upon the introduction of the dodecylguanidine formulation in water. The compatibility with anionic components in the aqueous formulation is improved.

To improve their suspension in water, dispersants are frequently added to the active ingredient formulations, such as dodine WP and WP formulations. Frequently used dispersants are alkylnaphtalene sulphonates, for instance sodium diisopropylnaphtalene sulphonate and sodium alkylnaphtalene sulphonate, and lignosulphonate, such as sodium lignosulphonate.

Whereas the combination of these dispersants with a carboxylic acid salt of dodecylguanidine needed to be avoided as they could lead to incompatibility problems when added to water, these problems can now be overcome by their combination with the compatibility agent. In a preferred embodiment of an agrochemical composition of the invention, the composition further comprises an anionic surfactant, preferably an alkylnaphtalene sulphonate and/or lignosulphonate.

Alternatively, the compatibility agent can be added to an aqueous tank-mix comprising dodecylguanidine or a salt, ester or derivative thereof and further comprising an ingredient that is incompatible with the dodecylguanidine or a salt, ester or derivative thereof.

By the term "tank-mix" as used herein, is meant the addition of at least one agrochemical active ingredient to a spray medium, such as water or oil, at the point of use.

In a second aspect, the invention provides a tank-mix prepared by mixing water, an agrochemical composition comprising a carboxylic acid salt of dodecylguanidine, a compatibility agent for slowing down the dissociation reaction of the carboxylic acid salt of dodecylguanidine in an aqueous medium thereby suppressing or preventing the formation of anionic dodecylguanidine, and an active ingredient selected from the list of pesticides, fertilizers, biocides and combinations thereof, characterized in that, the ratio of the dodecylguanidine acetate to the alkali metal acetate anion or earth alkali metal acetate anion in the tank-mix is below 5.0, preferably between 3.0 and 0.5, more preferably equals 1.4.

In a preferred embodiment of a tank-mix of the invention, the carboxylic acid salt of dodecylguanidine is dodecylguanidine acetate (dodine). In a preferred embodiment of the tank-mix of the invention, the compatibility agent is an alkali metal acetate or earth alkali metal acetate, preferably sodium acetate. In a more preferred embodiment the carboxylic acid salt of dodecylguanidine is dodecylguanidine acetate (dodine) and the compatibility agent is sodium acetate.

A combination of a carboxylic acid salt of dodecylguanidine, preferably dodecylguanidine acetate (dodine), with one or more of the pesticide active ingredients spirodiclofen, pyrimethanil and methoxyfenozide is not possible due to incompatibility problem.

Spirodiclofen is an acaricidal active ingredient from the chemical class of tetronic acids, that inhibits lipid biosynthesis. It has an activity against many economically important mite species infesting a broad range of perennial crops, such as spider mites (Tetranychidae), gall- or rust mites (Eriophyidae) and false spider mites (Tenuipalpidae). The basic formulation is a 240 g/l soluble concentrate (SC) formulation.

Pyrimethanil or N-(4,6-dimethylpyrimidin-2-yl)aniline is a foliar fungicide for preharvest control of certain plant diseases on almonds, pistachios, bulb vegetables, grapes, stone fruits (except cherries), pome fruits, potatoes and other tuberous and corm vegetables, strawberries and tomatoes. Pyrimethanil is the class of chemistry called anilinopyrimidines (fungicides). This class acts to inhibit the secretion of fungal enzymes which are required during the infection process, blocking the ability of fungi to degrade and digest the plant tissues, thus stopping penetration and development of the disease. Pyrimethanil formulations are marketed under the trade names Clarinet®, Mythos®, Scala®, Siganex®, Vision®, Walabi®. The basic formulation is a soluble concentrate (SC) formulation.

Methoxyfenozide or benzoic acid, 3-methoxy-2-methyl-, 2-(3,5-dimethylbenzoyl)-2-(1,1-dimethylethyl)hydrazide, is an insect growth regulator, belonging to the diacylhydrazine class of insecticides, effective against species of Lepidopteran insects such as beet armyworm, yellow striped armyworm, saltmarsh caterpillar, soybean looper and fall armyworm. It does not disrupt beneficial insects, mites and pollinators. This makes it suitable for integrated pest management programs. Methoxyfenozide formulations are marketed under the trade names Intrepid®. Formulations are available as flowable concentrate (F) and as powder in a water soluble pouch (WSP).

The inventors have found that the addition of the compatibility agent of the invention, in particular sodium acetate, improves the compatibility of the carboxylic acid salt of dodecylguanidine with the pesticide active ingredients spirodiclofen, pyrimethanil and methoxyfenozide. A compatible tank-mix is provided. In a preferred embodiment of a tank-mix of the invention, the active ingredient is a pesticide selected from the list of spirodiclofen, pyrimethanil and methoxyfenozide. It is advantageous to be able to combine dodine with these active ingredients. The combination saves time as separate application of the active ingredients becomes unnecessary. A field only needs to be entered once. The soil is less compacted.

In a preferred embodiment of the tank-mix of the invention, the anionic surfactant comprises an alkylnaphtalene sulphonate, preferably sodium diisopropylnaphtalene sulphonate or sodium alkylnaphtalene sulphonate, or a lignosulphonate, preferably sodium lignosulphonate.

In a preferred embodiment of the tank-mix of the invention, the dodine formulation added to the tank-mix is an agrochemical composition comprising a carboxylic acid salt of dodecylguanidine, preferably dodine, according to an embodiment of the invention. These formulations have the advantage that the compatibility agent is already built in. No calculation is required to obtain a correct ratio of compatibility agent versus dodecylguanidine salt.

In another aspect the invention provides a method for preparing an aqueous tank-mix of a carboxylic acid salt of dodecylguanidine, comprising the steps of: adding a carboxylic acid salt of dodecylguanidine to a spray tank holding water, and adding to the aqueous mixture an active ingredient selected from the list of pesticides, fertilizers, biocides and combinations thereof, to obtain an aqueous tank-mix. A method according to an embodiment of the invention is characterized in that the method further comprises the step of: adding to the tank an amount of compatibility agent for slowing down the dissociation of the carboxylic acid salt of dodecylguanidine to form anionic dodecylguanidine, wherein the amount of compatibility agent is selected so that the ratio of the dodecylguanidine acetate to that of the compatibility agent is below 5.0, preferably between 3.0 and 0.5, more preferably equals 1.4.

In a preferred embodiment of the method of the invention, the carboxylic acid salt of dodecylguanidine is dodecylguanidine acetate (dodine) and the compatibility agent is an alkali metal acetate or earth alkali metal acetate, preferably sodium acetate.

In a final aspect, the invention provides use of an alkali metal acetate or earth alkali metal acetate for improving the compatibility of a carboxylic acid salt of dodecylguanidine with an additional pesticide and/or fertilizer in an aqueous medium.

In a preferred aspect of the use, the tank-mix further comprises an anionic surfactant, preferably a lignosulphonate or an alkylnaphtalene sulphonate The invention is further described by the following non-limiting examples which further illustrate the invention, and are not intended to, nor should they be interpreted to, limit the scope of the invention.

It is supposed that the present invention is not restricted to any form of realization described previously and that some modifications can be added to the presented example of fabrication without reappraisal of the appended claims. For example, the present invention has been described referring to acetate of dodecylguanidine, but it is clear that the invention can be applied to salts of dodecylguanidine for instance or to mixtures of acetate of dodecylguanidine with other active ingredients.

EXAMPLES

Examples 1-5

The dodine formulations listed in Table 1 below are prior art formulations (Examples 1-2) and formulations according to the invention (Examples 3-5).

Examples 1 to 4 are wettable granules. In the prior art examples of examples 1 and 2, the ratio of dodine to sodium acetate is 6.3 and 5.24 respectively. In the wettable granule formulations of Example 3 and 4, which are embodiments of the invention, the ratio of dodine to sodium acetate is 3.49 and 1.03 respectively. The suspension concentrate of Example 5 also has a dodine to sodium acetate ratio of 1.03.

TABLE 1

Comparative example - Compatibility tests

| Ingredient | Example 1 (prior art) Dodine 65 WG g/kg | Example 2 (prior art) Dodine 65 WG g/kg | Example 3 (invention) Dodine 65 WG g/kg | Example 4 (invention) Dodine 40WG g/kg | Example 5 (invention) Dodine 200SC g/l |
|---|---|---|---|---|---|
| Dodine technical grade 97%-98% | 663.3 | 663.3 | 663.3 | 412.4 | 204 |
| Dodine acetate | 650 | 650 | 650 | 400 | 200 |
| Sodium acetate anhydrous (filler, compatibility agent) | 106 | 126.7 | 190.0 | 400.0 | 200 |
| Acetate anion | 76.3 | 94 | 136.7 | 287.8 | 143.9 |
| Sodium diisopropylnaphthalene sulphonate (wetting agent) | 10 | | | | |
| Sodium alkylnaphtalene sulphonate | | 20 | | | |
| Ethoxylated alkylamine | | | | | 30.0 |
| Alkoxylated fatty alcohol | | 120 | 90 | 120.0 | |
| Dispersing agent | 120 | | | | |
| Antifoaming agent | | | | | 10.0 |
| Coadjuvant | 20 | | | | |
| Filler | 168.7 | 50 | 41.7 | 52.6 | |
| Thickener | | | | | 2.5 |
| Antifreeze | | | | | 30.0 |

TABLE 1-continued

Comparative example - Compatibility tests

| Ingredient | Example 1 (prior art) Dodine 65 WG g/kg | Example 2 (prior art) Dodine 65 WG g/kg | Example 3 (invention) Dodine 65 WG g/kg | Example 4 (invention) Dodine 40WG g/kg | Example 5 (invention) Dodine 200SC g/l |
|---|---|---|---|---|---|
| Biocide | | | | | 1.0 |
| Residual water | | 20.0 | 15.0 | 15.0 | remainder |
| Ratio dodine/sodium acetate | 6.3 | 5.24 | 3.49 | 1.03 | 1.03 |
| Ratio dodine acetate/acetate anion | 8.52 | 6.91 | 4.75 | 1.39 | 1.39 |

Example 6

Tank-Mix Formulations Comprising Dodine without (Examples A-E in Table 2) and with Acetate (Examples A'-E' in Table 3)

Tank-mixes comprising dodine without acetate were prepared. The set-up of the experiment and results are summarized in Table 2. The mixtures were prepared by filling a tank with 200 l of water, adding dodine 400 SC to the water in a dose rate of 1.25 l per 200 l, adding another pesticide (A, B, D, E) or adjuvant (C) to the aqueous dodine mixture and mixing the tank-mix thus obtained for 30 minutes. Mixing was stopped. The behavior of the spray-mix was observed for any indications of incompatibility (settling, foaming, clump or gel formation).

It was observed that when the pesticide selected was spirodiclofen, pyrimethanil and methoxyfenozide in the form of their commercial products as indicated in the Table 2, it was shown that obtaining a homogeneous mixture without the requirement for stirring, was not possible due to incompatibility problems with dodine.

As a comparison, the same tank-mixes were prospered, this time comprising dodine with acetate (A'-E'). The mixtures were prepared by filling a tank with 200 l of water, adding Dodine 400 SC to the water in a dose rate of 1.25 l/200 l, adding another pesticide (A', B', D', E') or adjuvant (C') to the aqueous dodine mixture, adding 0.36 kg/200 l sodium acetate, and homogenizing the tank-mixes thus obtained by further mixing. Mixing was stopped after 30 minutes. The behavior of the tank-mix was observed for any indications of incompatibility (settling, foaming, clump or gel formation). The results are summarized in Table 3.

It was observed that the addition of sodium acetate improved the compatibility of dodine with the other selected pesticides, in particular spirodiclofen, pyrimethanil and methoxyfenozide. The pesticides were used in the form of their commercially available products as indicated in Table 3. Except for methoxyfenozide and copper oxychloride, constant agitation to keep dodine from settling to the bottom of the tank was not required.

The addition of 0.36 kg acetate to an aqueous mixture of 1.25 l dodine 400 SC in 200 l water comprising 1 liter of the wetting agent known under the tradename Adhasit remarkably improved the compatibility of dodine with the wetting agent.

TABLE 2

Tank-mixtures comprising dodine 400 SC (1.25 l/200 l) and another pesticide or adjuvant without compatibility agent.

| Product code | Product | Dose rate (liter/hectare) | Active ingredient | Water (liter) | Compatibility test |
|---|---|---|---|---|---|
| A | Envidor | 0.4 | Spirodiclofen | 200 | Not compatible |
| B | Scala SC | 0.75 | Pyrimethanil | 200 | Not compatible |
| C | Adhasit | 1 | Wetting agent | 200 | Constant agitation required |
| D | Funguran | 3 | Copper oxychloride | 200 | Not compatible |
| E | Runner | 0.4 | Methoxyfenozide | 200 | Not compatible |

TABLE 3

Tank-mixtures comprising dodine 400 SC (1.25 l/200 l), another pesticide or adjuvant and sodium acetate (0.36 kg/200 l).

| Product code | Product | Dose rate (liter/hectare) | Active ingredient | Water (liter) | Compatibility test |
|---|---|---|---|---|---|
| A' | Envidor | 0.4 | Spirodiclofen | 200 | Compatible |
| B' | Scala | 0.75 | Pyrimethanil | 200 | Compatible |
| C' | Adhasit | 1 | Wetting agent | 200 | Compatible |
| D' | Funguran | 3 | Copper oxychloride | 200 | Constant agitation required |
| E' | Runner | 0.4 | Methoxyfenozide | 200 | Constant agitation required |

Example 7

Three experiments were set up according to the following protocol: A receptacle capable of holding 100 ml water is selected. 50 ml of water is introduced to the receptacle. A sulphur formulation is added to the water and stirred. A formulation based on dodine is then added. The mixture thus obtained is stirred. 50 ml of water are added. The stirring is stopped. The mixture is observed after 30 minutes.

In a first experiment (7.1) the sulphur formulation was a micronized, wettable powder sulphur formulation (Microthiol 81 WP) at a dose rate of 5 kg/300 l. The dodine formulation is a dodine 40 WG formulation, comprising 400 g/kg sodium acetate. The formulation was added at a dose rate of 1.7 kg/300 l. After 30 minutes, a homogeneous brown-colored mixture was observed.

In a second experiment (7.2) the protocol of the experiment 7.1 was followed, but the sulphur formulation of experiment 7.1 was replaced with a wettable granule called Necator 80 WG (5 kg/300 l). After 30 minutes, a homogeneous white-colored mixture was observed.

In a third experiment (7.3) the protocol of experiment 7.1 was followed, but the dodine formulation was replaced with a dodine 400 SC formulation, comprising 400 g/l dodine without the presence of sodium acetate. After 30 minutes, two layers were observed in the mixture. A dark-brown coloured top layer and a light-brown bottom layer. The mixture was not compatible.

Example 8

Half of the total amount of water a selected receptacle can hold is introduced in the receptacle. A tebuconazole formulation (9.6 l Savannah/1500 l) is added to the receptacle and mixed. Dodine 400 SC is added at a dose rate of 15.6 l/1500 l and the mixture obtained is stirred. The other half of the water is added. The mixture is observed after 30 minutes.

What is claimed is:

1. An agrochemical composition comprising dodecylguanidine acetate (dodine) and a compatibility agent for slowing down the dissociation reaction of dodine in an aqueous medium thereby suppressing or preventing the formation of anionic dodecylguanidine, wherein the compatibility agent is an alkali metal acetate or earth alkali metal acetate, and the ratio of the dodecylguanidine acetate to that of the compatibility agent in the composition is from 0.5 to 5.0 and wherein the agrochemical composition is in the form of wettable granules or a wettable powder.

2. The agrochemical composition according to claim 1, wherein the compatibility agent is sodium acetate.

3. The agrochemical composition according to claim 1, wherein the composition further comprises an anionic surfactant.

4. A tank-mix prepared by mixing the composition of claim 1 with water and an active ingredient selected from the group consisting of pesticides, fertilizers, biocides and combinations thereof.

5. The tank-mix according to claim 4, wherein the compatibility agent is sodium acetate.

6. The tank-mix according to claim 4, wherein the active ingredient is a pesticide selected from the group consisting of spirodiclofen, pyrimethanil and methoxyfenozide.

7. The tank-mix according to claim 4, wherein the composition further comprises an anionic surfactant.

8. The tank-mix according to claim 7, wherein the anionic surfactant comprises an alkylnaphthalene sulphonate or a lignosulphonate.

9. A method for preparing an aqueous tank-mix of dodine, comprising the steps of:
adding the agrochemical composition of claim 1 to a spray tank holding water to form an aqueous mixture, and
adding to the aqueous mixture an active ingredient selected from the group consisting of pesticides, fertilizers, biocides and combinations thereof, to obtain an aqueous tank-mix.

10. The method according to claim 9, wherein the compatibility agent is sodium acetate.

11. The method according to claim 9, wherein the tank-mix further comprises a lignosulphonate or an alkylnaphthalene sulphonate.

12. The agrochemical composition according to claim 1, wherein the ratio of dodine to of the compatibility agent is from 0.5 to 3.0.

13. The agrochemical composition according to claim 1, wherein the ratio of dodine to compatibility agent equals 1.4.

14. The agrochemical composition according to claim 3, wherein the anionic surfactant comprises an alkylnaphthalene sulphonate.

15. The tank-mix according to claim 4, wherein the ratio of dodine to the alkali metal acetate anion or earth alkali metal acetate anion in the tank-mix is from 0.5 to 3.0.

16. The tank-mix according to claim 4, wherein the ratio of dodine to the alkali metal acetate anion or earth alkali metal acetate anion in the tank-mix equals 1.4.

17. The method according to claim 9, wherein the ratio of dodine to the compatibility agent is from 0.5 to 3.0.

18. The method according to claim 9, wherein the ratio of dodine to the compatibility agent equals 1.4.

* * * * *